(12) United States Patent
Berzosa Rodríguez et al.

(10) Patent No.: US 10,723,721 B2
(45) Date of Patent: Jul. 28, 2020

(54) PROCESS FOR PREPARING AND PURIFYING THE LFA-1 ANTAGONIST LIFITEGRAST

(71) Applicant: INTERQUIM, S.A., Sant Cugat del Vallès (ES)

(72) Inventors: Xavier Berzosa Rodríguez, Terrassa (ES); Francisco Marquillas Olondriz, Barcelona (ES)

(73) Assignee: INTERQUIM, S.A., Sant Cugat del Vallès (ES)

( * ) Notice: Subject to any disclaimer, the term of this patent is extended or adjusted under 35 U.S.C. 154(b) by 0 days.

(21) Appl. No.: 16/632,057

(22) PCT Filed: Jul. 23, 2018

(86) PCT No.: PCT/EP2018/069949
§ 371 (c)(1),
(2) Date: Jan. 17, 2020

(87) PCT Pub. No.: WO2019/020580
PCT Pub. Date: Jan. 31, 2019

(65) Prior Publication Data
US 2020/0148670 A1  May 14, 2020

(30) Foreign Application Priority Data

Jul. 24, 2017 (EP) .................................... 17382487

(51) Int. Cl.
*C07D 405/06* (2006.01)
*C07D 217/02* (2006.01)

(52) U.S. Cl.
CPC ......... *C07D 405/06* (2013.01); *C07D 217/02* (2013.01)

(58) Field of Classification Search
CPC ............................ C07D 405/06; C07D 217/02
USPC ....................................................... 546/139
See application file for complete search history.

(56) References Cited

U.S. PATENT DOCUMENTS

| 8,080,562 B2* | 12/2011 | Burnier ..................... A61K 9/08 514/307 |
| 9,085,553 B2* | 7/2015 | Zeller ................... C07D 405/06 |
| 2011/0092707 A1* | 4/2011 | Burnier ................ C07D 405/10 546/146 |

FOREIGN PATENT DOCUMENTS

| WO | WO 2005/044817 A1 | 5/2005 | |
| WO | WO-2009013987 A1 * | 1/2009 | ............... C11D 3/28 |
| WO | WO 2009/139817 A2 | 11/2009 | |
| WO | WO 2011/050175 A1 | 4/2011 | |
| WO | WO-2014018748 A1 * | 1/2014 | ........... C07D 405/06 |

OTHER PUBLICATIONS

International Search Report for PCT/EP2018/069949 (PCT/ISA/210) dated Nov. 19, 2018.
Written Opinion of the International Searching Authority for PCT/EP2018/069949 (PCT/ISA/237) dated Nov. 19, 2018.

* cited by examiner

*Primary Examiner* — Rita J Desai
(74) *Attorney, Agent, or Firm* — Birch, Stewart, Kolasch & Birch, LLP

(57) ABSTRACT

The invention relates to a process for the preparation of lifitegrast (I) comprising a) reacting benzofuran-6-carboxylic acid (II) with a non-chlorinated carboxyl activating agent; and b) reacting the activated compound obtained in step a) with compound (III) or a salt thereof to give lifitegrast. It also relates to a process for the purification of lifitegrast (I) by i) reacting lifitegrast with dicyclohexylamine to give the dicyclohexylamine salt of lifitegrast (Ia); ii) isolating the salt from the reaction medium; iii) converting the isolated salt into lifitegrast by treatment with an acid; and iv) isolating lifitegrast from the reaction medium. It also relates to the dicyclohexylamine salt of lifitegrast (Ia) and to a process for its preparation. (Formula I, III)

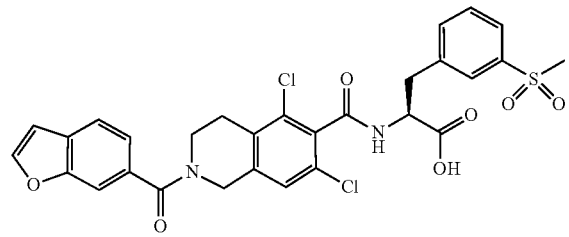

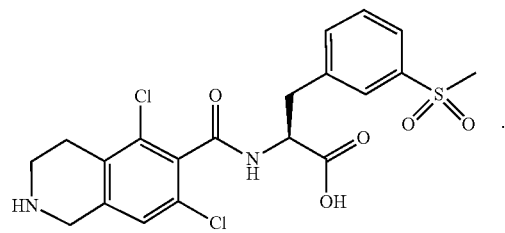

8 Claims, No Drawings

PROCESS FOR PREPARING AND PURIFYING THE LFA-1 ANTAGONIST LIFITEGRAST

TECHNICAL FIELD

The present invention relates to a process for the preparation of lifitegrast or a pharmaceutically acceptable salt thereof, and to a process for its purification. It also relates to the dicyclohexylamine salt of lifitegrast.

BACKGROUND ART

Lifitegrast is the generic name of compound of formula (I) (S)-2-(2-(benzofuran-6-carbonyl)-5,7-dichloro-1,2,3,4-tetrahydroisoquinoline-6-carboxamido)-3-(3-(methylsulfonyl)phenyl)-propanoic acid.

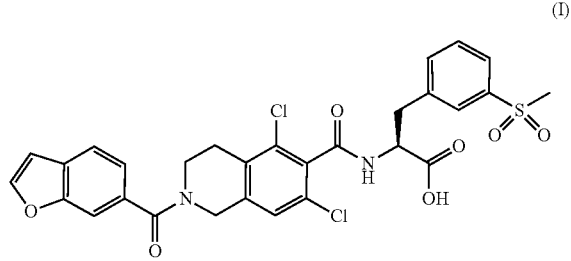 [SMILES: CS(=O)(=O)c1cccc(C[C@H](NC(=O)c2c(Cl)cc3c(c2Cl)CCN(C(=O)c2ccc4ccoc4c2)C3)C(=O)O)c1]

(I)

Lifitegrast is a lymphocyte function-associated antigen 1 antagonist (LFA-1) that has been approved by the US Food and Drug Administration (FDA) in the form of ophthalmic solution for the treatment of signs and symptoms of dry eye disease.

Lifitegrast was first described in the patent family including WO2006/125119. However, this PCT application does not disclose any preparation process for this active compound. WO2009/139817 describes a process for the preparation of lifitegrast shown in scheme 1. This process includes obtaining intermediate 19 by reacting a benzyl-protected compound 12 with the acyl chloride of acid 18, and subsequently removing the benzyl group by Pd-catalyzed hydrogenation to give lifitegrast (1):

Scheme 1

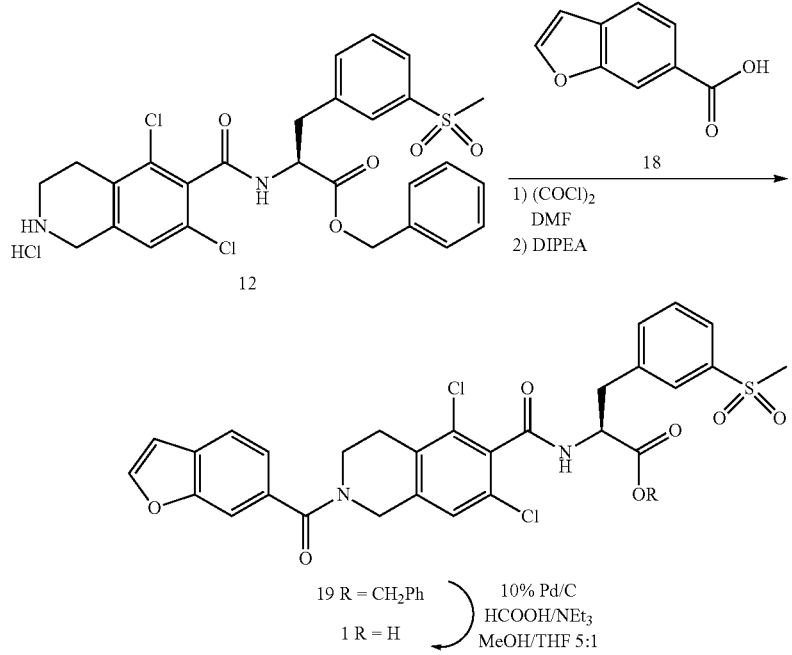

WO2011/050175 describes a process for the preparation of lifitegrast including obtaining intermediate 19 as described in WO2009/139817 and later removing the benzyl group by acid or basic hydrolysis.

Finally, WO2014/018748 describes a process for the preparation of lifitegrast including obtaining intermediate 19 as described in WO2009/139817 and later removing the benzyl group by phase transfer catalyst (biphasic conditions). WO2014/018748 also discloses the use of thionyl chloride ($SOCl_2$) and N-Methylmorpholine (NMM) as alternative conditions for the preparation of the acyl chloride of 18.

Concerning the purification of lifitegrast, WO2009/139817 discloses a step of slurrying lifitegrast in methyl ethyl ketone (MEK) or acetonitrile to give lifitegrast Form A. In WO2011/050175 and WO2014/018748 it is specified that the crystallization from MEK is carried out with seed crystals of 99% purity and 99% ee. The optical purity reported for the resulting lifitegrast in these conditions is of 97.9%.

The preparation of lifitegrast according to the previous processes shows some drawbacks. In particular, toxic chlorinating reagents are used which is disadvantageous per se. In addition, these toxic substances and potentially genotoxic chlorinated impurities resulting from the use of these reagents must be removed from the final product until below the maximum limit permissible in the product for regulatory reasons, which signifies hard purifications. Further, attempts to reproduce the crystallization of lifitegrast in MEK of the prior art failed in the hands of the inventors when using a crude product with 98% purity. In fact, there is no disclosure in the prior art documents as to how to achieve the seed crystal used in the purification step having 99% purity and 99% ee.

Therefore, a need exists of providing alternative processes for the preparation of lifitegrast that are reproducible, easy to industrialize, and avoid the prior art problems.

SUMMARY OF INVENTION

The inventors have developed a process for the preparation of lifitegrast or a pharmaceutically acceptable salt thereof that allows having a final product free of potentially genotoxic chlorinated impurities by avoiding the use of toxic and corrosive chlorinating agents. Additionally, if desired, the enantiomeric purity of lifitegrast may also be improved by purifying it via the formation of its dicyclohexylamine salt so that an enantiomeric excess up to 99.8% can be obtained. Furthermore, the processes of the invention are performed in good yield and are easy to industrialize.

Therefore, a first aspect of the invention relates to a process for the preparation of a compound of formula (I), lifitegrast,

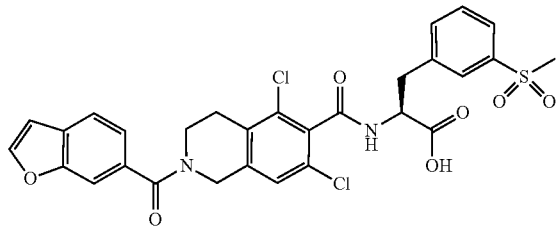
(I)

comprising the following steps:
a) reacting a compound of formula (II):

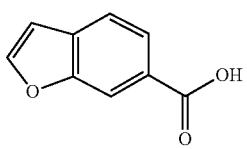
(II)

with a non-chlorinated carboxyl activating agent in the presence of an appropriate solvent to give an activated derivative of the compound of formula (II);

b) reacting the activated compound of formula (II) obtained in step a) with a compound of formula (III) or a salt thereof in the presence of an appropriate solvent and optionally in the presence of a base

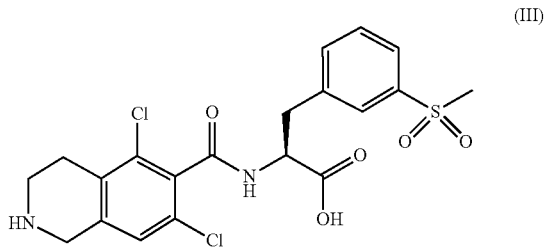 [SMILES: CS(=O)(=O)c1cccc(C[C@H](NC(=O)c2c(Cl)cc3c(c2Cl)CCNC3)C(=O)O)c1]
(III)

to give a compound of formula (I); and c) optionally isolating the obtained compound of formula (I).

Another aspect of the invention relates to a process for purifying lifitegrast comprising the following steps:

i) reacting the compound of formula (I) with dicyclohexylamine (DCHA) in the presence of an appropriate solvent to give a compound of formula (Ia);

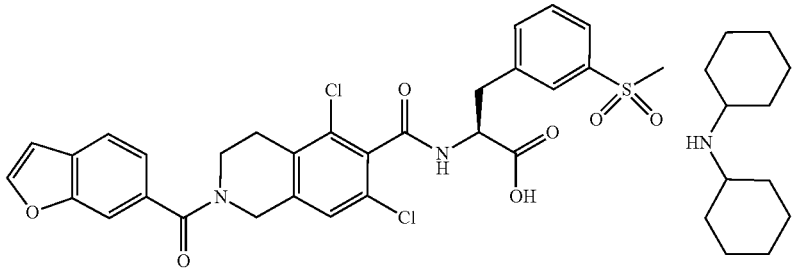
(Ia)

ii) isolating the compound of formula (Ia) from the reaction medium;
iii) converting the compound of formula (Ia) obtained in the previous step into a compound of formula (I) by treatment with an acid in the presence of an appropriate solvent; and
iv) isolating the compound of formula (I) from the reaction medium.

A third aspect of the invention relates to a compound of formula (Ia) as defined above.

It is also part of the invention a process for the preparation of a compound of formula (Ia) comprising the reaction of a compound of formula (I) with dicyclohexylamine (DCHA) in the presence of an appropriate solvent.

DETAILED DESCRIPTION OF THE INVENTION

All terms as used herein in this application, unless otherwise stated, shall be understood in their ordinary meaning as known in the art. Other more specific definitions for certain terms as used in the present application are as set forth below and are intended to apply uniformly through-out the specification and claims unless an otherwise expressly set out definition provides a broader definition.

For the purposes of the invention, room temperature is 20-25° C.

The term "enantiomeric excess" or ee as used herein refers to a difference between the amount of one enantiomer and the amount of the other enantiomer that is present in the product mixture. It can be calculated by using the following formula:

$$ee(\%) = \left\{\frac{(x-y)}{(x+y)}\right\} \cdot 100$$

wherein x and y are the relative amounts of the two enantiomers, which can be measured by chiral HPLC. Thus, for example, a product mixture having 98% of one enantiomer and 2% of the other enantiomer has an enantiomeric excess of 96%.

The terms "HPLC purity" and "HPLC chiral purity" as used herein refer to the percentage of peak area that is subject to HPLC detection and then area normalization according to the obtained chromatogram in the total peak area.

The present invention relates to processes for preparing and purifying lifitegrast (Compound of formula (I)). It is also contemplated in the present invention that lifitegrast as obtained in the processes disclosed herein is optionally converted into a pharmaceutically acceptable salt thereof by treatment with a base in the presence of an appropriate solvent.

There is no limitation on the type of salts that can be used, provided that these are pharmaceutically acceptable when they are used for therapeutic purposes, i.e. they have the desired activity and are non-toxic or of acceptable toxicity at the dosage levels envisaged. The term "pharmaceutically acceptable salt", embraces salts commonly used to form addition salts of the free acid of lifitegrast.

The preparation of pharmaceutically acceptable salts of lifitegrast (I) can be carried out by methods known in the art. For instance, they can be prepared from the parent compound, which contains an acidic moiety, by conventional chemical methods.

In the first aspect of the invention, the process of preparing lifitegrast comprises a first step a) of reacting a compound of formula (II) with a non-chlorinated carboxyl activating agent. Non-limiting examples of non-chlorinated carboxyl activating agents include 1,1'-carbonyldiimidazole (CDI), 1,1'-carbonyl-di-(1,2,4-triazol) (CDT), dicyclohexylcarbodiimide (DCC), diisopropylcarbodiimide (DIC), N-(3-dimethylamino-propyl)-N'-ethylcarbodiimide (EDC), and a combination of one of the previous with N-hydroxysuccinimide or N-hydroxyphthalimide, benzotriazol-1-yloxy-tris(dimethylamino)-phosphonium hexafluorophosphate (BOP), bromo-tripyrrolidino-phosphonium hexafluorophosphate (PyBrOP), benzotriazol-1-yloxy-tripyrrolidinophosphonium hexafluoro-phosphate (PyBOP), 2-(1H-benzotriazol-1-yl)-N,N,N',N'-tetramethylaminium tetrafluoroborate (TBTU), 2-(1H-benzotriazol-1-yl)-N,N,N',N'-tetramethylaminium hexafluorophosphate (HBTU), 2-(7-aza-1H-benzotriazol-1-yl)-N,N,N',N'-tetramethyl-aminium hexafluorophosphate (HATU), and 2-(7-aza-1H-benzotriazol-1-yl)-N,N,N',N'-tetramethylaminium tetrafluoroborate (TATU).

In a particular embodiment, optionally in combination with one or more features of the various embodiments described above or below, the non-chlorinated carboxyl activating agent is selected from the group consisting of: CDI, CDT, DCC, DIC, EDC, and a combination of one of the previous with N-hydroxysuccinimide or N-hydroxyphthalimide, BOP, PyBrOP, PyBOP, TBTU, HBTU, HATU, and TATU. More particularly, the non-chlorinated carboxyl activating agent is CDI or CDT, and even more particularly is CDI.

As a result of the reaction of compound (II) with the non-chlorinated carboxyl activating agent as defined above, an activated derivative of the compound of formula (II) is obtained. For example, when the non-chlorinated carboxyl activating agent is CDI or CDT, activated derivative of the compound of formula II has the formula (IIa):

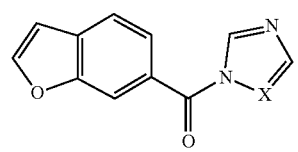

(IIa)

wherein X is C when the non-chlorinated carboxyl activating agent is CDI, and X is N when the non-chlorinated carboxyl activating agent is CDT.

Step a) is carried out in the presence of an appropriate solvent. In one particular embodiment, optionally in combination with one or more features of the various embodiments described above or below, the solvent is selected from dimethylsulfoxide (DMSO), dimethylformamide (DMF), dimethylacetamide (DMA), tetrahydrofuran (THF), acetone, methyl ethyl ketone (MEK), methyl isobutyl ketone (MIK), dichloromethane (DCM), acetonitrile (ACN), and mixtures thereof; more particularly, the solvent is DMSO.

In another particular embodiment, optionally in combination with one or more features of the various embodiments described above or below, step a) is carried out at a temperature comprised between room temperature and the temperature of the boiling point of the solvent, more particularly at a temperature comprised from 20 to 70° C., even more particularly at a temperature comprised from 50 to 70° C. or 20 to 25° C.

The process of the first aspect of the invention comprises a second step b) of reacting the activated carboxylic acid compound obtained in step a), with a compound of formula (III) or a salt thereof to give a compound of formula (I).

Step b) is carried out in the presence of an appropriate solvent. In a particular embodiment, optionally in combination with one or more features of the various embodiments described above or below, the solvent is selected from dimethylsulfoxide (DMSO), dimethylformamide (DMF), dimethylacetamide (DMA), tetrahydrofuran (THF), acetone, methyl ethyl ketone (MEK), methyl isobutyl ketone (MIK), dichloromethane (DCM), acetonitrile (ACN), and mixtures thereof; more particularly, the solvent is DMSO or a mixture of DMSO and DCM.

Step b) is carried out optionally in the presence of a base. Non limiting examples of bases that can be used are triethylamine, diisopropylethylamine (DIPEA), N-methylmorpholine (NMM), and dimethylaminopiridine (DMAP).

In a particular embodiment, optionally in combination with one or more features of the various embodiments described above or below, step b) is carried out in the absence of a base.

In another particular embodiment, optionally in combination with one or more features of the various embodiments described above or below, step b) is carried out in the presence of a base selected from the group consisting of triethylamine, DIPEA, NMM, and DMAP, more particularly triethylamine.

In another particular embodiment, optionally in combination with one or more features of the various embodiments described above or below, step b) is carried out at a temperature comprised between room temperature and the temperature of the boiling point of the solvent, more particularly, at room temperature.

In another particular embodiment, optionally in combination with one or more features of the various embodiments described above or below, step b) is carried out at a temperature comprised between −5° C. and the temperature of the boiling point of the solvent, more particularly, between 0-5° C.

The above described process comprising steps a) and b) has the advantage that the chlorine-free carboxyl activating agent cannot generate chlorinated impurities that could be genotoxic. Thus, the lifitegrast obtained by the preparation process of the invention is free from chlorinated impurities unlike in the prior art processes where the reaction of compound (II) with thionyl chloride generate chlorinated impurities. Without being bound to theory, it is believed that these chlorinated impurities are formed by the introduction of Cl in the benzofuran ring of the lifitegrast molecule.

Further, the coupling reaction of the activated compound (II) and the compound of formula (III) gave unexpectedly compound (I) in good yield despite of the possible side reactions due to the presence of the free carboxylic acid in compounds of formula (III). Thus, under the conditions of the process of the invention the amide derivative resulting from the intermolecular reaction of two compounds of formula (III) is not formed and the coupling reaction results in good yields.

In the reaction of step b) the compound of formula (III) can be used in neutral form or in the form of a salt, which can be either an acid addition salt with the amine present in the compound of formula (III), or a basic addition salt with the carboxylic acid present in the compound of formula (III).

The "acid addition salt" of the compound of formula (III) as used herein refers to any salt formed by the addition of an organic or inorganic acid to the compound of formula (III). Illustrative inorganic acids which form suitable salts include, without limitation, hydrochloric acid, hydrobromic acid, sulfuric acid, nitric acid, phosphoric acid and the like. Illustrative organic acids which form suitable salts include, without limitation, formic acid, acetic acid, propionic acid, oxalic acid, succinic acid, maleic acid, salicylic acid, methanesulfonic acid, ethanesulfonic acid, trifluoromethanesulfonic acid, benzenesulfonic acid, p-toluenesulfonic acid, p-chlorobenzenesulfonic acid, p-bromobenzenesulfonic acid, phthalic acid, isophthalic acid, benzoic acid, and the like.

The "basic addition salt" as used herein means any salt formed by the addition of an organic or inorganic base to the compound of formula (III). Illustrative inorganic bases which form suitable salts include without limitation lithium, sodium, potassium, calcium, magnesium aluminium, zinc or barium hydroxide. Illustrative organic bases which form suitable salts include aliphatic, alicyclic or aromatic organic amines such as methylamine, triethylamine, diisopropylethylamine, picoline, ammonia, ethylenediamide, ethanolamine, N,N-dialkylenethanolamine, diethanolamine, triethanolamine, glucamine, triethylamine, dicyclohexylamine, cyclohexylamine, imidazole, pyridine, and basic amino acids.

In a particular embodiment, optionally in combination with one or more features of the various embodiments described above or below, the compound of formula (III) used in step b) is an acid addition salt of the compound of formula (III). More particularly, the compound of formula (III) used in step b) is in the form of its hydrochloride salt.

In another particular embodiment, optionally in combination with one or more features of the various embodiments described above or below, the compound of formula (III) used in step b) is a basic addition salt of the compound of formula (III). More particularly, the compound of formula (III) used in step b) is in the form of its triethylamine, diisopropylethylamine, pyridine or its imidazole salt; even more particularly, the compound of formula (III) used in step b) is in the form of its imidazole or triethylamine salt.

The obtained lifitegrast resulting from step b) is optionally isolated from the reaction medium in step c). For example, lifitegrast can be crystallized or precipitated in a solvent or mixture of solvents and separated from the reaction medium, e.g. by filtration or centrifugation.

In any of the crystallization processes of any compounds disclosed in the present invention, non-limiting examples of solvents that can be used include hexane, benzene, toluene, 1,4-dioxane, chloroform, diethyl ether, methyl tert-butyl ether (MTBE), dichloromethane (DCM), tetrahydrofuran (THF), ethyl acetate (EtOAc), isopropyl acetate (IPrOAc), acetone, dimethylformamide (DMF), acetonitrile (ACN), dimethylsulfoxide (DMSO), n-butanol, isopropanol (IPA), n-propanol, ethanol, methanol, water or combinations thereof. Moreover, to induce the crystallization process of the desired product, in case it has not taken place during the reaction, there are several options, e.g., the solution can be cooled down to low temperatures, e.g. 0° C., other solvents may be added, or if the product is available, it can be seeded to facilitate the crystallization. Generally, the products may be precipitated or crystallized at a temperature that may range from 0° C. to 30° C.

Thus, in one particular embodiment, optionally in combination with one or more features of the various embodiments described above or below, step c) comprises the crystallization or precipitation of lifitegrast in a solvent selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof, more particularly, in a mixture of DMSO and water, in a mixture of acetone and MTBE, or in a mixture of DCM and IPrOAc; and even more particularly in a mixture of DMSO and water.

In step b) of the process above, the compound of formula (III) may be prepared by processes well known in the art, such as for example the ones described in WO2009/139817, WO2011/050175, and WO2014/018748. The compound of formula (II) is commercially available or can be prepared by standard synthetic processes.

For example, in one particular embodiment, optionally in combination with one or more features of the various embodiments described above or below, the compound of formula (III) can be obtained by removing the protective group of a compound of formula (IV) or a salt thereof:

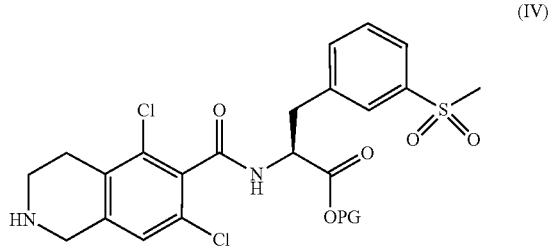

(IV)

wherein PG is a carboxy protective group.

Thus, in one embodiment, the invention relates to a process for the preparation of a compound of formula (I) as defined above, comprising the following steps a) to c) as previously defined further comprising previous to step b) the step a1) of removing the protective group of a compound of formula (IV) as defined above or a salt thereof to give a compound of formula (III) or its salt.

For the purposes of the invention, "protective group" (PG) refers to a grouping of atoms that when attached to a reactive group in a molecule masks, reduces or prevents that reactivity. Examples of suitable carboxy protective groups include, but are not limited to, silyl-, alkyl-, alkenyl-, aryl-, and arylalkyl- groups. Examples of suitable silyl groups include trimethylsilyl, triethylsilyl, t-butyldimethylsilyl, t-butyldiphenylsilyl, triisopropylsilyl, and the like. Examples of suitable alkyl groups include methyl, benzyl, p-methoxybenzyl, 3,4-dimethoxybenzyl, trityl, t-butyl, tetrahydropyran-2-yl. Examples of suitable alkenyl groups include allyl. Examples of suitable aryl groups include optionally substituted phenyl, biphenyl, or naphthyl. Examples of suitable arylalkyl groups include optionally substituted benzyl (e.g., p-methoxybenzyl (MPM), 3,4-dimethoxybenzyl, O-nitrobenzyl, p-nitrobenzyl, p-halobenzyl, 2,6-dichlorobenzyl, p-cyanobenzyl), and 2- and 4-picolyl.

The carboxy protective group can be removed by standard methods well-known in the art as described for example in T. W. Green and P. G. M. Wuts, Protective Groups in Organic Chemistry (Wiley, 3rd ed. 1999, Chapter 5, pp. 369-451).

In a particular embodiment, optionally in combination with one or more features of the various embodiments described above or below, in the compound of formula (IV) PG is benzyl. In one more particular embodiment, the removal of the benzyl group is carried out by acidic hydrolysis, i.e., by the treatment with an acid and optionally in the presence of a solvent. Alternatively, in another more particular embodiment, the removal of the benzyl group is carried out by basic hydrolysis, i.e., in the presence of a base and optionally in the presence of a solvent. The hydrolysis (either under acidic or basic conditions) is carried out at a temperature comprised between room temperature and the temperature of the boiling point of the solvent.

Non-limiting examples of solvents that can be used in the hydrolysis reaction include hexane, benzene, toluene, 1,4-dioxane (also referred herein to as dioxane), chloroform, diethyl ether, methyl tert-butyl ether (MTBE), dichloromethane (DCM), tetrahydrofuran (THF), ethyl acetate (EtOAc), isopropyl acetate (IPrOAc), acetone, dimethylformamide (DMF), acetonitrile (ACN), dimethylsulfoxide (DMSO), n-butanol, isopropanol (IPA), n-propanol, ethanol, methanol, water, and mixtures thereof.

Non-limiting examples of acids that can be used in the acidic hydrolysis include HCl, $H_2SO_4$, $H_3PO_4$, formic acid, acetic acid or trifluoroacetic acid. Non-limiting examples of bases that can be used in the basic hydrolysis include NaOH, KOH or LiOH.

In a particular embodiment, optionally in combination with one or more features of the various embodiments described above or below, in the compound of formula (IV) PG is benzyl, and the removal of the benzyl group is carried out by acidic hydrolysis in the presence of aqueous HCl at the reflux temperature.

In a particular embodiment, optionally in combination with one or more features of the various embodiments described above or below, in the compound of formula (IV) PG is benzyl, and the removal of the benzyl group is carried out by acidic hydrolysis in the presence of aqueous HCl or HCl (g) at a temperature comprised between room temperature and the reflux temperature, more particularly at room temperature.

In another particular embodiment, optionally in combination with one or more features of the various embodiments described above or below, in the compound of formula (IV) PG is benzyl, and the removal of the benzyl group is carried out by basic hydrolysis in the presence of NaOH and an appropriate solvent, as for example toluene, dioxane, dimethylsulphoxide (DMSO) or water, and mixtures thereof; at a temperature between room temperature and boiling temperature of the solvent or the mixture of solvents, preferably at a temperature comprised from 60 to 80° C.

If desired, the compound of formula (III) obtained from the compound of formula (IV) can be isolated from the reaction medium. For example the compound of formula (III) can be isolated in the form of a salt, by addition of an acid or a base (if necessary) to the reaction medium.

In one embodiment, the compound of formula (III) may be isolated in the form of a basic addition salt of the compound of formula (III) by reacting the compound of formula (III) with an amine, in particular an amine selected from triethylamine, diisopropylethylamine, pyridine and imidazole, even more particularly, imidazole or triethylamine; in the presence of an appropriate solvent and isolating it from the reaction medium.

In a more particular embodiment, the isolation of the addition salt of the compound of formula (III) is carried by crystallization or precipitation in a solvent or mixture of solvents, more particularly in a solvent selected from dimethylsulfoxide (DMSO), dimethylformamide (DMF), dichloromethane (DCM), and mixtures thereof, and separated from the reaction medium, e.g. by filtration or centrifugation.

It also forms part of the invention a compound of formula (IIIa)

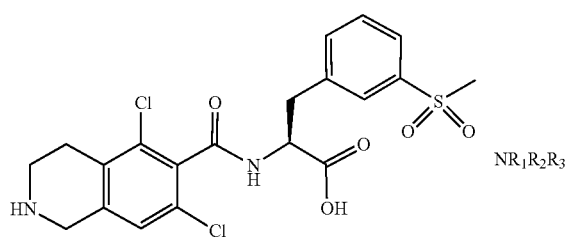

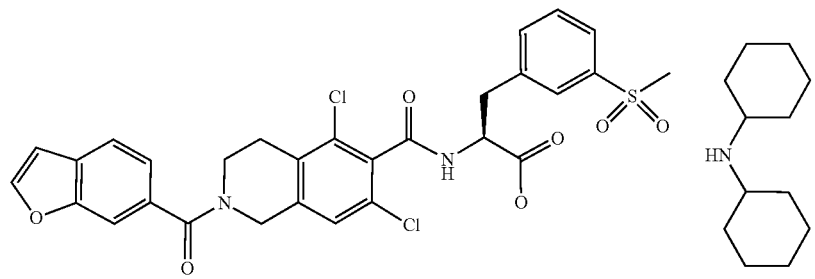

wherein NR₁R₂R₃ is an amine selected from the group consisting of triethylamine, diisopropylethylamine, pyridine and imidazole.

Alternatively, the compound of formula (III) or its salt can be used directly without having been isolated from the reaction mixture after removal of the protecting group for the compound of formula (IV).

In another embodiment, the invention relates to a process for the preparation of a compound of formula (I) as defined above, comprising the following steps:
a) reacting a compound of formula (II) as defined above with a non-chlorinated carboxyl activating agent, more particularly a non-chlorinated carboxyl activating agent selected from the group consisting of: CDI, CDT, DCC, DIC, EDC, and a combination of one of the previous with N-hydroxysuccinimide or N-hydroxyphthalimide, BOP, PyBrOP, PyBOP, TBTU, HBTU, HATU, and TATU; even more particularly, CDI or CDT, and even more particularly CDI; in the presence of an appropriate solvent, particularly selected from DMSO, DMF, DMA, THF, acetone, MEK, MIK, DCM, ACN, and mixtures thereof; and more particularly DMSO, to give an activated derivative of the compound of formula (II);
b) reacting the activated compound of formula (II) obtained in step a), with a compound of formula (III) as defined above or a salt thereof, in the presence of an appropriate solvent, particularly selected from DMSO, DMF, DMA, THF, acetone, MEK, MIK, DCM, ACN, and mixtures thereof; and more particularly DMSO or a mixture of DMSO and DCM, and optionally in the presence of a base, particularly a base selected from the group consisting of triethylamine, DIPEA, NMM, and DMAP, more particularly in the absence of a base; to give a compound of formula (I); and
c) optionally isolating the obtained compound of formula (I) as obtained in step b) from the reaction medium, in particular by crystallization or precipitation in a solvent selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof, more particularly, in a mixture of DMSO and water, in a mixture of acetone and MTBE, or in a mixture of DCM and IPrOAc; and even more particularly in a mixture of DMSO and water.

The present invention also relates to a process for the purification of lifitegrast as mentioned in the second aspect of the invention. This process comprises the step i) of reacting the compound of formula (I) with dicyclohexylamine (DCHA) in the presence of an appropriate solvent to give a compound of formula (Ia)

Non-limiting examples of solvents that can be used in the in step i) include hexane, benzene, toluene, 1,4-dioxane, chloroform, diethyl ether, methyl tert-butyl ether (MTBE), dichloromethane (DCM), tetrahydrofuran (THF), ethyl acetate (EtOAc), isopropyl acetate (IPrOAc), acetone, methylethylketone (MEK), methyl isobutyl ketone (MIK), dimethylformamide (DMF), dimethylacetamide (DMA), acetonitrile (ACN), dimethylsulfoxide (DMSO), n-butanol, isopropanol (IPA), n-propanol, ethanol, methanol, water or combinations thereof.

In one embodiment, optionally in combination with one or more features of the various embodiments described above or below, the solvent used in step i) is selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof; more particularly is either THF, or MEK, or a mixture of acetone and MTBE, or a mixture of acetone and water; preferably a mixture of acetone and water.

In another embodiment, optionally in combination with one or more features of the various embodiments described above or below, the amount of solvent used in step i) is from 4 to 10 volumes.

In another embodiment, optionally in combination with one or more features of the various embodiments described above or below, the amount of DCHA used in step i) is from 0.9 to 5 equivalents, more particularly from 0.9 to 1.5 equivalents.

In another embodiment, optionally in combination with one or more features of the various embodiments described above or below, the amount of DCHA used in step i) is the amount needed to reach a pH 8.2 to 9.5, more preferably a pH 8.2 to 8.3.

As illustrated in the examples of the invention, the purification of lifitegrast via the dicyclohexylamine salt allows improving the chemical purity and enantiomeric excess in the final product. In one embodiment, the enantiomeric excess of lifitegrast is equal or higher than 96%, equal or higher than 98%, equal or higher than 99%. In another embodiment, the enantiomeric excess of lifitegrast is 99.5%. In another embodiment, the enantiomeric excess of lifitegrast is 99.8%. In another embodiment, the enantiomeric excess of lifitegrast is 99.9%.

Step i) is preferably carried out at a temperature comprised between 0° C. and the temperature of the boiling point of the solvent, particularly, at a temperature from 0° C. to room temperature. In one embodiment, optionally in combination with one or more features of the various embodiments described above or below, step i) is carried out at room temperature.

The lifitegrast used as starting lifitegrast in step i) can be used directly without having been isolated from a previous reaction or can be a product that has been isolated and optionally purified, for example by the crystallization or slurrying process as indicated below.

Thus, in one particular embodiment, optionally in combination with one or more features of the various embodiments described above or below, the starting lifitegrast in step i) is used directly without having been isolated as a solid before performing the purification process.

The starting lifitegrast of step i) may be obtained by the preparation process of the invention previously described. Thus, in one embodiment, optionally in combination with one or more features of the various embodiments described above or below, the process of purification further comprises the following steps a) to c) before step i):

a) reacting a compound of formula (II) as previously defined with a non-chlorinated carboxyl activating agent in the presence of an appropriate solvent to give an activated derivative of the compound of formula (II);

b) reacting the activated compound of formula (II) obtained in step a), with a compound of formula (III) as previously defined or a salt thereof in the presence of an appropriate solvent and optionally in the presence of a base to give a compound of formula (I); and c) optionally isolating the lifitegrast obtained.

More particularly, in the above embodiment, step i) comprises reacting the compound of formula (I) obtained in step b) as a product without having been isolated with dicyclohexylamine (DCHA) in the presence of an appropriate solvent to give a compound of formula (Ia).

The particular conditions mentioned above for steps a), b) and c) of the preparation process also apply to this latter embodiment.

The obtained lifitegrast dicyclohexylamine salt (Ia) resulting from step i) is isolated from the reaction medium in step ii). For example the compound of formula (Ia) can be crystallized or precipitated in a solvent or mixture of solvents and separated from the reaction medium, e.g. by filtration or centrifugation.

Thus, in one particular embodiment, optionally in combination with one or more features of the various embodiments described above or below, step ii) comprises isolating the dicyclohexylamine salt (Ia) by precipitation or crystallization in a solvent selected from the group consisting of hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol, water or combinations thereof; more particularly, in MEK, or in a mixture of acetone and MTBE, or in a mixture of acetone and water, or in a mixture of THF and MTBE; preferably a mixture of acetone and water. More particularly, the mixture of acetone and MTBE is a mixture wherein the ratio between acetone and MTBE is from 2:1 to 10:1; the mixture of acetone and water is a mixture wherein the ratio between acetone and water is from 2:1 to 10:1; and the mixture of THF and MTBE is a mixture wherein the ratio between THF and MTBE is from 2:1 to 10:1.

In another embodiment, optionally in combination with one or more features of the various embodiments described above or below, the amount of solvent used in step ii) is from 4 to 10 volumes.

If desired, the dicyclohexylamine salt (Ia) obtained in step ii) can be purified before converting it into lifitegrast. For example, the compound of formula (Ia) can be slurried or recrystallized in a solvent or mixture of solvents, and separated from the reaction medium, e.g. by filtration or centrifugation. Thus, in one particular embodiment, optionally in combination with one or more features of the various embodiments described above or below, the process further comprises step ii1) of purifying the compound of formula (Ia) by slurrying or recrystallization in a solvent or mixture of solvents selected from the group consisting of hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol, water or combinations thereof; more particularly, in THF, ethanol or a mixture of ACN and methanol, or a mixture of IPrOAc and methanol. More particularly, the mixture of ACN and methanol is a mixture wherein the ratio between ACN and methanol is from 1:1 to 10:1, and the mixture of IPrOAc and methanol is a mixture wherein the ratio between iPrOAc and methanol is from 1:1 to 10:1.

In step iii) of the purification process, the dicyclohexylamine salt of formula (Ia) is converted into lifitegrast by the treatment with an acid and in the presence of a solvent. Non-limiting examples of solvents that can be used in the reaction include hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol water, or combinations thereof.

Non-limiting examples of acids that can be used in the reaction include HCl, $H_2SO_4$, $H_3PO_4$, formic acid, acetic acid or trifluoroacetic acid.

In one embodiment, optionally in combination with one or more features of the various embodiments described above or below, the salt of formula (Ia) is converted into a compound of formula (I) by the treatment with an acidic aqueous solution of HCl, $H_2SO_4$ or $H_3PO_4$, and in the presence of a solvent such as DCM.

In another particular embodiment, optionally in combination with one or more features of the various embodiments described above or below, step iii) is carried out at a temperature comprised between room temperature and the temperature of the boiling point of the solvent, more particularly at room temperature.

The obtained lifitegrast resulting from step iii) is isolated from the reaction medium in step iv). For example the compound of formula (I) can be crystallized or precipitated in a solvent or mixture of solvents and separated from the reaction medium, e.g. by filtration or centrifugation.

Seeds of crystalline lifitegrast may be added to the reaction medium to assist the crystallyzation of a preferred polymorph, as for example crystalline Form A.

Thus, in one embodiment, optionally in combination with one or more features of the various embodiments described above or below, step iv) comprises isolating the lifitegrast from the reaction medium by crystallization or precipitation in a solvent selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof, more particularly in a mixture of acetone and MTBE, or in a mixture of DCM and IPrOAc. Preferably lifitegrast is crystallized from a DCM reaction medium. More particularly, the mixture of acetone and MTBE is a mixture wherein the ratio between acetone and MTBE is from 1:5 to 1:20, and the mixture of DCM and IPrOAc is a mixture wherein the ratio between DCM and IPrOAc is from 1:5 to 1:20.

If desired, the obtained lifitegrast obtained in step iv) can be purified. For example, the compound of formula (I) can be slurried or recrystallized in a solvent or mixture of solvents, and separated from the reaction medium, e.g. by filtration or centrifugation. Thus, in one particular embodiment, optionally in combination with one or more features of the various embodiments described above or below, the purification process further comprises step iv1) of purifying the compound of formula (I) by slurrying or recrystallization in a solvent or mixture of solvents selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof, more particularly, in a mixture of DCM and IPrOAc. More particularly, the mixture of DCM and IPrOAc is a mixture wherein the ratio between DCM and IPrOAc is from 1:5 to 1:20.

In the process for the purification of lifitegrast defined in the second aspect of the invention, the formation of the dicyclohexylamine salt can be repeated more than once, particularly one time. Thus, steps i), ii) and iii) can be repeated before isolation of lifitegrast in step iv).

Thus, in one particular embodiment of the invention, optionally in combination with one or more features of the various embodiments described above or below, the process for purifying lifitegrast of formula (I), comprises the following steps:
i) reacting the compound of formula (I) with dicyclohexylamine (DCHA) in the presence of an appropriate solvent to give a compound of formula (Ia);
ii) isolating the compound of formula (Ia) from the reaction medium;
iii) converting the compound of formula (Ia) obtained in the previous step into a compound of formula (I) by treatment with an acid in the presence of an appropriate solvent;
iii1) optionally repeating steps i), ii) and iii)
and
iv) isolating the compound of formula (I) from the reaction medium.

In one particular embodiment of the later embodiment, steps i), ii) and iii) are repeated, more particularly steps i), ii) and iii) are repeated one time.

In another particular embodiment steps ii1) and iv1) are also included in the purification process.

The particular conditions mentioned above for steps i), ii) and iii) apply to this later embodiment.

The formation of the dicyclohexylamine salt (step i)) can be repeated using the same solvent or different solvents. For example, firstly, step i) can be performed by using a mixture of acetone and water, and then repeated by using a mixture of acetone and methyl tert-butyl ether (MTBE). Particularly, the same solvent is used; more particularly the solvent is acetone and water.

The most appropriate conditions under which the processes of the invention are carried out may vary depending on different parameters considered by those skilled in the art, such as the concentration of starting material, temperature, solvent used and the like. These parameters may be easily determined by those skilled in the art through routine testing and using the teachings in the examples of the present specification.

In one embodiment, the invention relates to a process for purifying lifitegrast of formula (I), comprising the following steps:
i) reacting the compound of formula (I) with dicyclohexylamine (DCHA) in the presence of an appropriate solvent, particularly a solvent selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof; more particularly is either THF, or MEK, or a mixture of acetone and MTBE, or a mixture of acetone and water; to give the dicyclohexylamine salt of lifitegrast of formula (Ia);
ii) isolating the dicyclohexylamine salt (Ia) from the reaction medium, in particular by precipitation or crystallization in a solvent selected from the group consisting of hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol, water or combinations thereof; more particularly, in MEK, or in a mixture of acetone and MTBE, or in a mixture of acetone and water, or in a mixture of THF and MTBE; preferably in a mixture of acetone and water.
ii1) optionally purifying the compound of formula (Ia), in particular by slurrying or by recrystallization in a solvent or mixture of solvents, more particularly selected from the group consisting of hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol, water or combinations thereof; more particularly, in THF, ethanol or a mixture of ACN and methanol, or a mixture of IPrOAc and methanol;
iii) converting the compound of formula (Ia) obtained in the previous step into a compound of formula (I) by the treatment with an acid, more particularly an acid selected from the group consisting of HCl, $H_2SO_4$, $H_3PO_4$, formic acid, acetic acid and trifluoroacetic acid, in the presence of an appropriate solvent, particularly a solvent selected from the group consisting of hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol, and water, more particularly DCM;
iv) isolating the compound of formula (I) from the reaction medium, in particular by crystallization or precipitation in a solvent selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof; more particularly in a mixture of acetone and MTBE, or in a mixture of DCM and IPrOAc; preferably lifitegrast is crystallized from a DCM reaction medium; and
iv1) optionally purifying the compound of formula (I), in particular by slurrying it or by recrystallization in a solvent or mixture of solvents, more particularly selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof; even more particularly, in a mixture of DCM and IPrOAc.

In another embodiment, the invention relates to a process for the preparation and purification of lifitegrast of formula (I), comprising the following steps:
a) reacting a compound of formula (II) as defined above with a non-chlorinated carboxyl activating agent, more particularly a non-chlorinated carboxyl activating agent selected from the group consisting of: CDI, CDT, DCC, DIC, EDC, and a combination of one of the previous with N-hydroxysuccinimide or N-hydroxyphthalimide, BOP, PyBrOP, PyBOP, TBTU, HBTU, HATU, and TATU; even more particularly, CDI or CDT, and even more particularly CDI; in the presence of an appropriate solvent, particularly selected from DMSO, DMF, DMA, THF, acetone, MEK, MIK, DCM, ACN, and mixtures thereof; and more particularly DMSO, to give an activated derivative of the compound of formula (II);
b) reacting the activated compound of formula (II) obtained in step a), with a compound of formula (III) as defined above or a salt thereof, in the presence of an appropriate solvent, particularly selected from DMSO, DMF, DMA, THF, acetone, MEK, MIK, DCM, ACN, and mixtures thereof; and more particularly a mixture of DMSO and DCM, and optionally in the presence of a base, particularly a base selected from of a base selected from the group consisting of triethylamine, DIPEA, NMM, and DMAP, more particularly in the absence of a base; to give a compound of formula (I);
i) reacting the compound of formula (I) of the previous step without isolating it with dicyclohexylamine (DCHA) in the presence of an appropriate solvent, particularly a solvent selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof; more particularly is either THF, or MEK, or a mixture of acetone and MTBE, or a mixture of acetone and water; to give the dicyclohexylamine salt of lifitegrast of formula (Ia);
ii) isolating the dicyclohexylamine salt (Ia) from the reaction medium, in particular by precipitation or crystallization in a solvent selected from the group consisting of hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol, water or combinations thereof; more particularly, in MEK, or in a mixture of acetone and MTBE, or in a mixture of acetone and water, or in a mixture of THF and MTBE; preferably in a mixture of acetone and water.
ii1) optionally purifying the compound of formula (Ia), in particular by slurrying or by recrystallization in a solvent or mixture of solvents, more particularly selected from the group consisting of hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol, water or combinations thereof; more particularly, in THF, ethanol or a mixture of ACN and methanol, or a mixture of IPrOAc and methanol;
iii) converting the compound of formula (Ia) obtained in the previous step into a compound of formula (I) by the treatment with an acid, more particularly an acid selected from the group consisting of HCl, $H_2SO_4$, $H_3PO_4$, formic acid, acetic acid and trifluoroacetic acid, in the presence of an appropriate solvent, particularly a solvent selected from the group consisting of hexane, benzene, toluene, 1,4-dioxane, chloroform, diethyl ether, MTBE, DCM, THF, EtOAc, IPrOAc, acetone, MEK, DMF, ACN, DMSO, n-butanol, IPA, n-propanol, ethanol, methanol, and water, more particularly DCM;
iv) isolating the compound of formula (I) from the reaction medium, in particular by crystallization or precipitation in a solvent selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof; more particularly in a mixture of acetone and MTBE, or in a mixture of DCM and IPrOAc; preferably lifitegrast is crystallized from a DCM reaction medium; and
iv1) optionally purifying the compound of formula (I), in particular by slurrying it or by recrystallization in a solvent or mixture of solvents, more particularly selected from the group consisting of hexane, benzene, toluene, 1,4-dioxane, chloroform, diethyl ether, MTBE, DCM, THF, EtOAc, IPrOAc, acetone, DMF, ACN, DMSO, n-butanol, IPA, n-propanol, ethanol, methanol, water or combinations thereof; even more particularly, in a mixture of DCM and IPrOAc.

As mentioned above, the present invention also relates to a compound of formula (Ia) as previously defined and to a process for its preparation comprising the reaction of a compound of formula (I) with dicyclohexylamine (DCHA) in the presence of an appropriate solvent.

The particular conditions mentioned above for step i) of the purification process also apply to the process for the preparation of the compound of formula (Ia).

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

HPLC Method:
Chromatographic column: HSS PFP 100×2.1 mm×1.8 μm; Column temperature: 45° C.;
Mobile phase: A: Trifluoroacetic acid 0.10%, B: Acetonitrile
Gradient Elution Conditions:
The chromatograph is programmed as follows:

| Time (minutes) | Solution A (%) | Solution B (%) | Elution |
|---|---|---|---|
| 0 | 95 | 5 | Gradient |
| 0.43 | 95 | 5 | Isocratic |
| 10.72 | 10 | 90 | Isocratic |
| 12.78 | 95 | 5 | |
| Post-time: 1.03 | | | Re-equilibrate |

Main peak retention time: around 5.5 min; Sample volume 1 μL; Detection wavelength: 215 nm; running time: 12.43 min; Test solution: 1 mg/mL, Solvent: Acetonitrile: Milli-Q water (8:2); Column flow: 0.65 ml/min

Benzyl (S)-2-(5,7-dichloro-1,2,3,4-tetrahydroisoquinolin-6-carboxamido)-3-(3-(methylsulfonyl)phenyl) propanoate hydrochloride (Compound IV-HCl)

A) Preparation of Compound IV-HCl 2-(tert-Butoxycarbonyl)-5,7-dichloro-1,2,3,4-tetrahydroisoquinoline-6-carboxylic acid (5 g, 14.4 mmol) was dissolved in a mixture DMSO (25 mL) and triethylamine (10.1 mL, 72.2 mmol). HATU (6.9 g, 18.1 mmol) was added. The mixture was stirred at room temperature for 10 min. Benzyl (S)-2-amino-3-(3-(methylsulfonyl)phenyl) propanoate hydrochloride (5.9 g, 15.9 mmol) was added and the mixture was stirred for 18 h at room temperature. Isopropyl acetate (50 mL) and water (50 mL) were added. The phases were separated and the organic phase was washed with water (50 mL) and then with 1N HCl (50 mL). Dioxane (100 mL) was added and the isopropyl acetate was distilled. 4M HCl in dioxane (10 mL) was added and the mixture was stirred at room temperature for 30 min. The solid obtained was filtered, washed with dioxane, and dried in vacuo at 45° C. to give 8.69 g (99% yield) of the desired product (IV-HCl) as a white solid (HPLC purity: 97%).

B) Purification of Compound IV-HCl

Compound IV-HCl as obtained in the previous step (20 g, 33 mmol) was dissolved in a mixture of DCM (200 mL) and triethylamine (4.7 mL). The DCM phase was washed with water (200 mL). Dioxane (400 mL) was added and the DCM was distilled off. Then, 4M HCl in dioxane (10 mL) was added and the mixture was stirred at room temperature for 1.5 h. The solid obtained was filtered, washed with dioxane, and dried under vacuum at 45° C. to yield 19.5 g (98% yield) of the desired product (IV-HCl) as a white solid (HPLC purity: 99.4%).

(S)-2-(5-(7-dichloro-1,2,3,4-tetrahydroisoquinolin-6-carboxamido)-3-(3-(methyl-sulfonyl)phenyl)propanoic acid) hydrochloride (Compound III-HCl)

A) Preparation of Compound III-HCl by Acidic Hydrolysis

Example 1

Compound IV-HCl (19.5 g, 32.6 mmol) was suspended in 18% HCl (195 mL). The mixture was heated to reflux and stirred for 30 min. Then, it was cooled down to room temperature, and toluene (195 mL) was added. The phases were separated and the aqueous phase was washed with toluene (195 mL) and finally with dichloromethane (100 mL). The aqueous phase was evaporated to dryness and the solid obtained was suspended in ethanol (83 mL). The mixture was stirred for 10 min at 5° C., filtered and dried in vacuo at 45° C. to yield 13.2 g (80% yield) of the desired product (III-HCl) as a white solid (HPLC purity: 99%).

Example 2

A mixture of Compound IV-HCl (100 g, 167 mmol) and 700 mL of HCl 18% was heated to reflux. After 1 h of stirring the mixture was cooled down to 20-25° C. 200 mL of DCM were added. Phases were separated and aqueous phase was washed with 200 mL of DCM. Aqueous phase was distilled to almost dryness and then 250 mL of DMSO were added. Water was completely removed by distillation in presence of 500 mL of toluene. Toluene was also distilled and the solution of compound III-HCl in DMSO was used directly in the next step.

B) Preparation of Compound III-HCl by Basic Hydrolysis

Compound IV-HCl (0.2 g, 0.3 mmol) were suspended in 1N NaOH (1 mL). Toluene (1 mL) was added. The mixture was heated to 70° C. and stirred at that temperature for 2 h. The phases were separated, the aqueous phase is then acidified to acidic pH with 37% HCl, and was brought to dryness. A white solid mixture of compound III-HCl and NaCl was obtained (HPLC purity: 95%).

C) Preparation of the Imidazole Salt of the Compound of Formula (III)

Compound III-HCl as obtained in step A) (1 g, 2 mmol) was dissolved in DMSO (2 mL). Imidazole (0.33 g, 4.8 mmol) and later DCM (11 mL) were added. The solid obtained was filtered, washed with DCM and dried under vacuum. The obtained imidazole salt (0.8 g, 75% yield) showed 99% HPLC purity.

D) Preparation of the Triethylamine Salt of the Compound of Formula (III)

Compound III-HCl as obtained in step A) (1 g, 2 mmol) was dissolved in DMF (5 mL). Triethylamine (0.3 mL, 2.2 mmol) was added. The solid obtained was filtered, washed with DMF and dried in an oven at 45° C. under vacuum. The obtained triethylamine salt (1.01 g, 90% yield) showed 99% HPLC purity.

Lifitegrast (Compound I)

A) Preparation of benzofuran-6-yl(1H-imidazol-1-yl)methanone (Compound II-CDI)

Example 1

Benzofuran-6-carboxylic acid (Compound II, 3.8 g, 23.6 mmol) was dissolved in DMSO (50 mL). CDI (4 g, 24.6 mmol) was added and the mixture heated at 60° C. for 1 h. It was cooled down to room temperature. The obtained solution was used directly in the next step without further purification.

Example 2

Benzofuran-6-carboxylic acid (43.3 g, 267 mmol) was dissolved in DMSO (200 mL). CDI (43.3 g, 267 mmol) was added and the mixture is stirred at 20-25° C. for 1 h. BFCA-CDI solution in DMSO is used directly in the next step without further purification.

B) Preparation of Lifitegrast Dicyclohexylamine Salt (Compound (Ia))

Example 1

Compound III-HCl as obtained in step A)-example 1 (5 g, 9.8 mmol) was dissolved in DMSO (15 mL). The solution prepared in section A) was added dropwise at room temperature. The mixture was stirred at room temperature for 30 min. Water (50 mL) and DCM (50 mL) were added. The aqueous phase was extracted with additional DCM (50 mL). The organic phases were combined, acetone (20 mL) was added and the DCM was distilled off. The solution was filtered through a 0.2 μm filter. MTBE (10 mL) and dicyclohexylamine (2 mL, 10 mmol) were added and stirred at room temperature for 16 h. The mixture was cooled to 0° C. and stirred for 2 h. The solid was filtered and washed with MTBE, and dried at 45° C. in vacuo to give 5.5 g of yellowish solid (70% yield) (HPLC purity of 95%; HPLC chiral purity: 98%).

Example 2

Compound III-HCl (39 g, 77 mmol) was dissolved in DMSO (117 mL). A solution prepared as in A) but starting from 15 g of benzofuran-6-carboxylic acid was added dropwise at room temperature. The mixture was stirred at room temperature for 30 min. Separately, water (310 mL) was added to another recipient and 1N HCl (2 mL) was added to bring the pH to 2. To this mixture the DMSO solution was added dropwise adding at the same time 1N HCl to keep the pH around 2. The solid obtained was filtered and re-dissolved in a mixture of acetone (221 mL) and water (111 mL). DCHA (18 mL, 90 mmol) was added. The mixture was stirred at room temperature for 16 h. It was cooled to 0° C. and stirred at that temperature for 2 h. The solid obtained was filtered and washed with cold acetone. It was dried at 45° C. in vacuo to give 23.6 g of yellowish solid (39% yield) (HPLC purity: 98.5%; HPLC chiral purity: 99.9%).

Example 3

100 mL of DCM were added to the Compound III-HCl solution in DMSO as obtained in step A-example 2) and the mixture was cooled to 0-5° C. Benzofuran-6-carboxylic acid solution obtained in section A was added dropwise maintaining the temperature below 5° C. The mixture was stirred at 0-5° C. for 2 h.

After reaction completion 850 mL of water and 850 mL of DCM were added maintaining the temperature below 10° C. After phase separation the aqueous phase was extracted with 400 mL of DCM. Organic phases were mixed and washed three times with 400 mL of water. The organic phase was distilled to almost dryness, 470 mL of acetone were added and then the remaining DCM was distilled. The solution was filtered through a 0.2 μm filter. 240 mL of water were added and then dicyclohexylamine was added until pH=8.3. The mixture was stirred at 20-25° C. for 16 h and then cooled to 0-10° C. and stirred for additional 25 h. The product was filtered, then washed twice with 200 mL of water and dryed in the oven at 50° C.

Yield: 65%
HPLC purity: 99%
Chiral HPLC purity >99.5%

Example 4

Lifitegrast (2 g, 3.7 mmol) was dissolved in THF (20 mL). The solution was filtered through a 0.2 μm filter. DCHA (0.8 mL, 4 mmol) was added and the mixture was stirred for 24 h at room temperature. MTBE (4 mL) was added and it was stirred for 16 h at room temperature. The obtained solid was filtered and dried under study at 45° C. The obtained dicyclohexylamine salt of lifitegrast (1.8 g, 70% yield) showed 98.8% HPLC purity.

Example 5

Lifitegrast (1 g, 1.9 mmol) was dissolved in MEK (10 mL). DCHA (0.4 mL, 2 mmol) was added. The mixture was stirred for 5 h at room temperature. The obtained solid was filtered, washed with IPA and MTBE and dried in oven at 45° C. The obtained dicyclohexylamine salt of lifitegrast (0.8 g, 60% yield) showed 98.3% HPLC purity.

C) Purification of the Dicyclohexylamine Salt of Lifitegrast (Compound (Ia))

Example 1: Slurry in THF

Compound (Ia) (5.5 g, 6.9 mmol as obtained in example 1) was suspended in THF (110 mL) and stirred for 1 h at room temperature. The solid was filtered and dried at 45° C. under vacuum to give 4.5 g of yellowish solid (82% yield) (HPLC purity: 98%; HPLC chiral purity: 99%).

Example 2: Recrystallization from ACN/MeOH

Compound (Ia) (200 mg obtained as in example 1) were suspended in ACN (3 mL). The mixture was heated to reflux. MeOH (1 mL) was added. 2 mL of the solution were distilled off. It was cooled to room temperature. The solid obtained was filtered, washed with ACN and dried under vacuum at 45° C. The obtained dicyclohexylamine salt of lifitegrast (152 mg, 76% yield) showed 99.5% HPLC purity.

Example 3: Recrystallization from IPrOAc/MeOH

Compound (Ia) (24 g obtained as in example 1) was suspended in IPrOAc (360 mL). It was heated to reflux. MeOH was added (384 mL). 487 mL of the solution were distilled off. It was cooled to room temperature and stirred for 16 h. The solid obtained was filtered, washed with EtOAc and dried under vacuum at 45° C. The obtained dicyclohexylamine salt of lifitegrast (21 g, 88% yield) showed 99.3% HPLC purity.

Example 4: Conversion into Compound I and Formation of the Dicyclohexylamine Salt (Compound (Ia)

125 g of Lifitegrast dicyclohexylamine salt (Compound (Ia) as obtained in section B-Example 3 (157 mmol) were dissolved in a mixture of 1250 mL of DCM and 588 mL of 5% phosporic acid water solution. Phases were separated, the organic phase was distilled to almost dryness, 588 mL of acetone were added and then the remaining DCM was distilled. 300 mL of water were added and then dicyclohexylamine until pH=8.3. The mixture was stirred at 20-25° C. for 16 h and then cooled to 0-10° C. and stirred for 25 h more. The product was filtered, then washed twice with 200 mL of water and dryed in the oven at 50° C.

Yield: 85%
HPLC purity >99.5%
Chiral HPLC purity >99.9%

D) Preparation of Lifitegrast

Example 1

Compound (Ia) (22.5 g, HPLC purity: 98.6%) was dissolved in a mixture of DCM (112 mL) and 1% phosphoric acid water solution (112 mL). The phases were separated and the organic phase was washed 3 times with 1% phosphoric acid solution (112 mL). Acetone (90 mL) was added to the organic phase and DCM was distilled. The solution of the product in acetone was slowly added over MTBE (900 mL) precooled to 0° C., and stirred at 0° C. for 1 h. The solid was filtered and dried at 45° C. under vacuum to give 15 g of yellowish solid (86% yield) (HPLC purity: 98.2%; HPLC chiral purity: 99.9%).

Example 2

Compound (Ia) (114 g, 143 mmol) as obtained in section C-Example 4 were dissolved in a mixture of DCM (1140 mL) and 5% phosphoric acid water solution (71 mL). The solution was filtered through a 0.2 µm filter. 500 mL of 5% phosphoric acid water solution were added. The mixture was seeded with Lifitegrast Form A and stirred at 20-25° C. for 53 h. The product was filtered. Then, the solid was suspended in 1710 mL of 2% phosporic acid water solution and stirred at 50° C. for 0.5 h. The solid was filtered and the treatment was repeated four times. Finally the product is washed twice with 1710 mL of water and dryed in the oven at 50° C.

Yield: 96%
HPLC purity >99.5%
Chiral HPLC purity >99.9%

E) Recrystallization of Lifitegrast in DCM/IPrOAc

Lifitegrast (2 g) was dissolved in DCM (4 mL). The solution was added slowly over IPrOAc (40 mL). The solid obtained was filtered and dried at 45° C. under vacuum. The obtained lifitegrast (1.64 g, 82% yield) showed 98% HPLC purity.

CITATION LIST

WO2006/125119
WO2009/139817
WO2011/050175
WO2014/018748
T. W. Green and P. G. M. Wuts, Protective Groups in Organic Chemistry (Wiley, 3rd ed. 1999, Chapter 5, pp. 369-451).

The invention claimed is:

1. A process for the preparation of a compound of formula (I), (I)

[structure of Lifitegrast]

comprising the following steps:
a) reacting a compound of formula (II):

(II)

[structure of benzofuran-6-carboxylic acid]

with a non-chlorinated carboxyl activating agent in the presence of an appropriate solvent to give an activated derivative of the compound of formula (II);
b) reacting the activated compound of formula (II) obtained in step a), with a compound of formula (III) or a salt thereof in the presence of an appropriate solvent and optionally in the presence of a base (III)

[structure of compound III]

to give a compound of formula (I) or a salt thereof; and
c) optionally isolating the obtained lifitegrast.

2. The process according to claim 1, wherein the non-chlorinated carboxyl activating agent is selected from the group consisting of 1,1'-carbonyldiimidazole (CDI), 1,1'-carbonyl-di-(1,2,4-triazol) (CDT), dicyclohexylcarbodiimide (DCC), diisopropylcarbodiimide (DIC), N-(3-dimethylamino-propyl)-N'-ethylcarbodiimide (EDC), and a combination of one of the previous with N-hydroxysuccinimide or N-hydroxyphthalimide, benzotriazol-1-yloxy-tris (dimethylamino)-phosphonium hexafluorophosphate (BOP), bromo-tripyrrolidino-phosphonium hexafluorophosphate (PyBrOP), benzotriazol-1-yloxy-tripyrrolidino-phosphonium hexafluoro-phosphate (PyBOP), 2-(1H-benzotriazol-1-yl)-N,N,N',N'-tetramethylaminium tetrafluoroborate (TBTU), 2-(1H-benzotriazol-1-yl)-N,N,N'N'-tetramethylaminium hexafluorophosphate (HBTU), 2-(7-aza-1H-benzotriazol-1-yl)-N,N,N',N'-tetramethyl-aminium hexafluoro-phosphate (HATU), and 2-(7-aza-1H-benzotriazol-1-yl)-N,N,N',N'-tetramethylaminium tetrafluoroborate (TATU).

3. The process according to claim 2, wherein the non-chlorinated carboxyl activating agent is 1,1'-carbonyldiimidazole (CDI) or 1,1'-carbonyl-di-(1,2,4-triazol) (CDT).

4. The process according to claim 1, wherein step a) and b) are independently carried out in the presence of a solvent selected from dimethylsulfoxide (DMSO), dimethylformamide (DMF), dimethylacetamide (DMA), tetrahydrofuran (THF), acetone, methyl ethyl ketone (MEK), methyl isobutyl ketone (MIK), dichloromethane (DCM), acetonitrile (ACN), and mixtures thereof.

5. The process according to claim 1, wherein step a) is carried out at a temperature comprised from 20 to 25° C.

6. The process according to claim 1, wherein the process comprises a previous step of removing the protective group of a compound of formula (IV) or a salt thereof to yield the compound of formula (III):

(IV)

[structure of compound IV]

or a salt thereof, wherein PG is a carboxy protective group.

7. The process according to claim 6, wherein the compound of formula (III) or its salt is directly used in the next step without isolation.

8. The process according to claim 6, wherein the compound of formula (III) or its salt is isolated from the reaction medium before reacting it in the next step.

* * * * *